United States Patent

Teshigawara

(10) Patent No.: US 9,795,353 B2
(45) Date of Patent: Oct. 24, 2017

(54) X-RAY COMPUTED TOMOGRAPHY APPARATUS AND PHOTON COUNTING METHOD

(71) Applicant: TOSHIBA MEDICAL SYSTEMS CORPORATION, Otawara-Shi (JP)

(72) Inventor: Manabu Teshigawara, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 304 days.

(21) Appl. No.: 14/803,744

(22) Filed: Jul. 20, 2015

(65) Prior Publication Data

US 2015/0327827 A1 Nov. 19, 2015

Related U.S. Application Data

(63) Continuation of application No. PCT/JP2014/051355, filed on Jan. 23, 2014.

(30) Foreign Application Priority Data

Feb. 12, 2013 (JP) ................................ 2013-024742
Jan. 22, 2014 (JP) ................................ 2014-009879

(51) Int. Cl.
G01T 1/208 (2006.01)
A61B 6/00 (2006.01)
(Continued)

(52) U.S. Cl.
CPC ............ *A61B 6/5205* (2013.01); *A61B 6/032* (2013.01); *A61B 6/4241* (2013.01); *G01T 1/171* (2013.01);
(Continued)

(58) Field of Classification Search
None
See application file for complete search history.

(56) References Cited

U.S. PATENT DOCUMENTS 6,160,259 A 12/2000 Petrillo et al.
2011/0012014 A1* 1/2011 Livne ............... A61B 6/032
250/252.1
(Continued)

FOREIGN PATENT DOCUMENTS

JP 2003-43149 A 2/2003
JP 2012-13563 A 1/2012
WO WO 2009/115956 A2 9/2009

OTHER PUBLICATIONS

International Search Report dated Feb. 25, 2014 for PCT/JP2014/051355 filed on Jan. 23, 2014 (with English translation).
(Continued)

*Primary Examiner* — Hoon Song
(74) *Attorney, Agent, or Firm* — Oblon, McClelland, Maier & Neustadt, L.L.P.

(57) ABSTRACT

According to embodiment, an X-ray computed tomography apparatus includes an X-ray tube, an X-ray detector including a scintillator generating scintillation light upon incidence of X-ray photons and a photodetection element, a peak value detector detecting peak values corresponding to X-ray photons based on an output signal from the element, processing circuitry determining an attenuation characteristic of the light by each X-ray photon and an output decreased characteristic of the element, based on the values and time when each peak value was detected, correcting the detected values according to the characteristics, a counter counting the X-ray photons corresponding to the respective corrected peak values, wherein the processing circuitry reconstructs a medical image based on an output from the counter.

10 Claims, 5 Drawing Sheets

(51) Int. Cl.
*G01T 1/18* (2006.01)
*G01T 1/20* (2006.01)
*A61B 6/03* (2006.01)
*G01T 1/17* (2006.01)
*A61B 6/04* (2006.01)

(52) U.S. Cl.
CPC .............. *G01T 1/18* (2013.01); *G01T 1/2018* (2013.01); *A61B 6/0407* (2013.01); *A61B 6/54* (2013.01)

(56) References Cited

U.S. PATENT DOCUMENTS

| | | | | |
|---|---|---|---|---|
| 2011/0017918 | A1* | 1/2011 | Baeumer | G01T 1/17 250/370.11 |
| 2013/0223587 | A1* | 8/2013 | Moriyasu | A61B 6/03 378/5 |
| 2015/0327827 | A1* | 11/2015 | Teshigawara | A61B 6/032 378/19 |

OTHER PUBLICATIONS

International Written Opinion dated Feb. 25, 2014 for PCT/JP2014/051355 filed on Jan. 23, 2014.

* cited by examiner

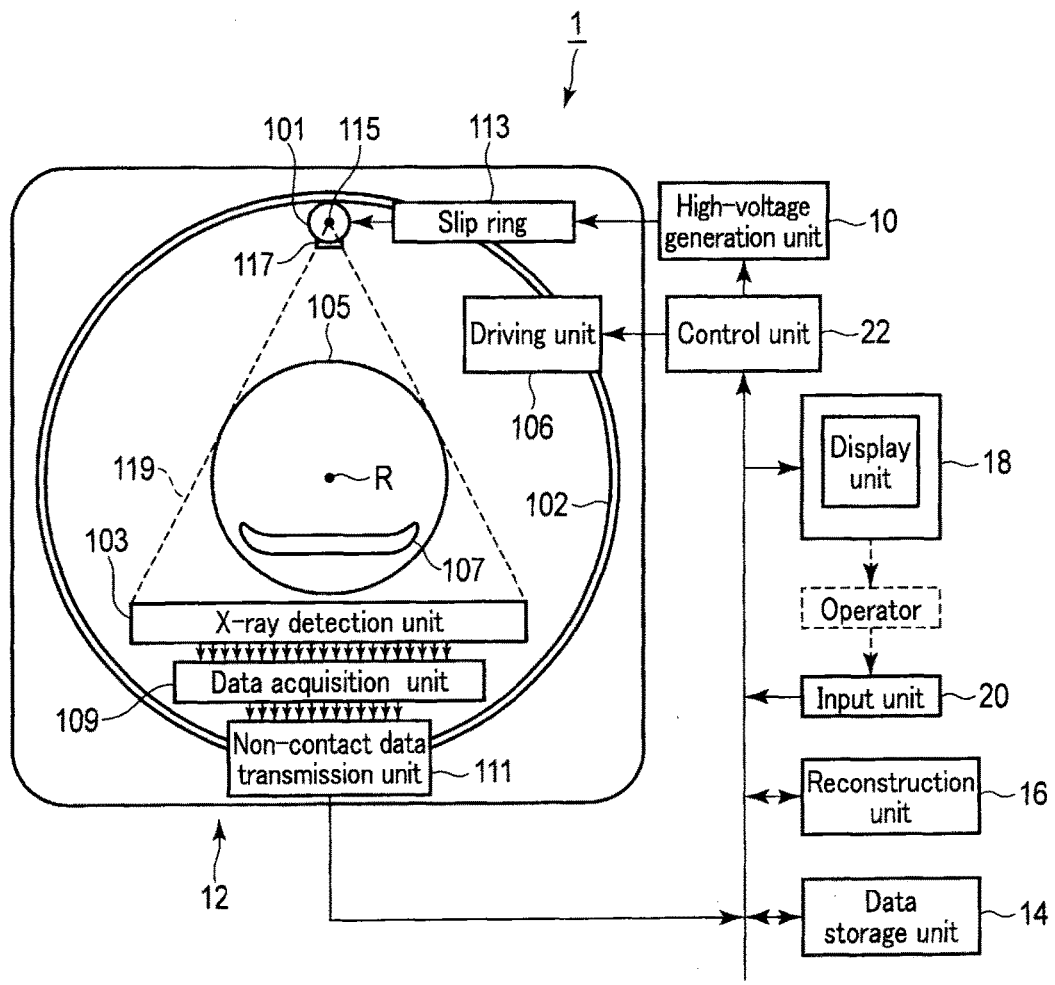
F I G. 1

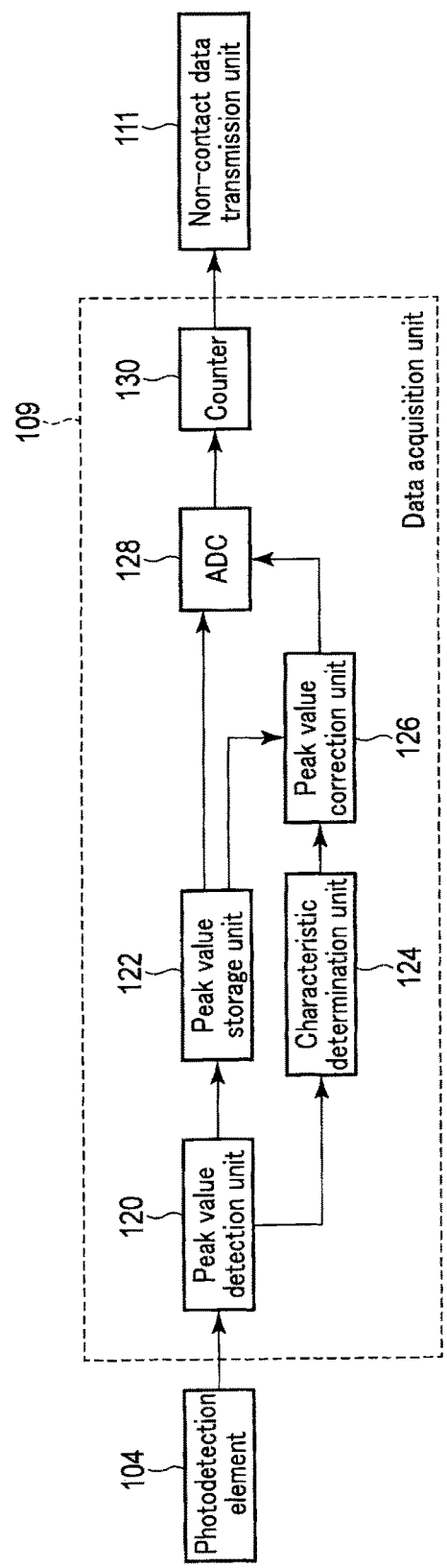
F I G. 2

X-RAY COMPUTED TOMOGRAPHY APPARATUS AND PHOTON COUNTING METHOD

CROSS-REFERENCE TO RELATED APPLICATIONS

This application is a Continuation application of PCT Application No. PCT/JP2014/051355, filed Jan. 23, 2014 and based upon and claims the benefit of priority from the Japanese Patent Application No. 2013-024742, filed Feb. 12, 2013 and the Japanese Patent Application No. 2014-009879, filed Jan. 22, 2014, the entire contents of all of which are incorporated herein by reference.

FIELD

Embodiments described herein relate generally to an X-ray computed tomography apparatus and a photon counting method.

BACKGROUND

There is an X-ray computed tomography apparatus (to be referred to as a photon counting X-ray CT apparatus hereinafter) that reconstructs an image regarding an object based on the number of photons of X-rays in an output from an X-ray detector. Performance requested of the X-ray detector of the photon counting X-ray CT apparatus is a high counting rate (the ratio of the number of detected photons to the number of photons entering the X-ray detector). The high counting rate is, e.g., a counting rate of about $10^6$ per 1 $mm^2$. For example, a semiconductor detector of CZT (CdZnTe: cadmium zinc telluride) or CdTe (cadmium telluride) has been prototyped as the X-ray detector. In order to obtain a high counting rate, the semiconductor detector is devised to decrease the light receiving area of each or a plurality of semiconductor elements in the semiconductor detector.

However, the semiconductor detector causes electrical polarization owing to repetitive incidence of X-ray photons. This puts a problem that the performance of the semiconductor detector changes.

Another X-ray photon detection method is a method of combining a scintillator and a photodetector. The method of combining a scintillator and a photodetector is free from the polarization problem, unlike the semiconductor detector. However, this method has a problem that output electrical signals overlap each other owing to generation of an incidence event by another X-ray photon during the emission time (typically about $40 \times 10^{-9}$ s) of the scintillator. In addition, when the next X-ray photon enters during charging of the photodetector, an output signal becomes weaker than an output signal upon incidence of a single X-ray photon, failing in obtaining a proper energy integrated value. These problems are specific to the method of combining a scintillator and a photodetector, and are called pile-up.

BRIEF DESCRIPTION OF THE DRAWINGS

FIG. 1 is a view showing an example of the arrangement of an X-ray computed tomography apparatus according to an embodiment.

FIG. 2 is a block diagram showing an example of the arrangement of a data acquisition unit according to the embodiment.

DETAILED DESCRIPTION

Figure 3:
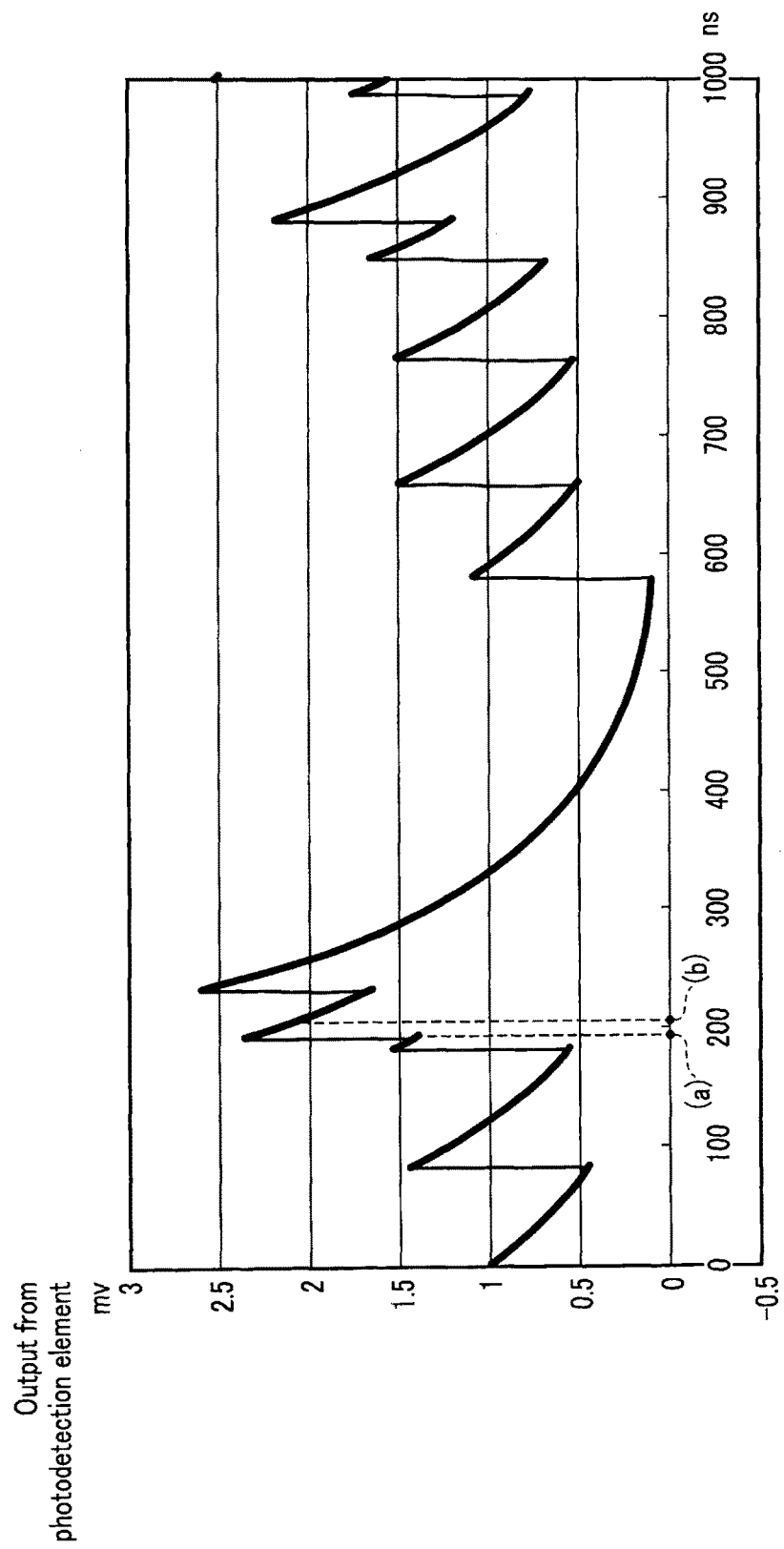
FIG. 3 is a graph showing an example of pile-up according to the embodiment.

In general, according to one embodiment, an X-ray computed tomography apparatus includes an X-ray tube, an X-ray detector, a peak value detector, processing circuitry, and a counter.

The X-ray tube generates an X-ray.

The X-ray detector includes a scintillator generating scintillation light upon incidence of X-ray photons that have been generated from the X-ray tube and have passed through an object, and a photodetection element provided on a rear surface of the scintillator;

The peak value detector detects peak values corresponding to respective X-ray photons entering the scintillator based on an output signal from the photodetection element.

The processing circuitry determines an attenuation characteristic of the scintillation light by each of the X-ray photons and an output decreased characteristic of the photodetection element, based on the peak values and time when each of the plurality of peak values was detected, and corrects the detected peak values in accordance with the attenuation characteristic and the output decreased characteristic.

The counter configured to count the numbers of X-ray photons corresponding to the respective corrected peak values.

The processing circuitry reconstructs a medical image based on an output from the counter.

An embodiment of an X-ray computed tomography apparatus based on photon counting will now be described with reference to the accompanying drawings. In the following description, the same reference numerals denote building components having almost the same functions and arrangements, and a repetitive description will be made only when necessary.

FIG. 1 is a view showing an example of the arrangement of an X-ray computed tomography apparatus according to the embodiment. An X-ray computed tomography apparatus 1 includes a high-voltage generation unit 10, a gantry 12, a data storage unit 14, a reconstruction unit 16, a display unit 18, an input unit 20, and a control unit 22.

The high-voltage generation unit 10 includes a high-voltage power supply and a filament current generator (neither is shown). The high-voltage power supply applies a high voltage between the anode target and cathode filament of an X-ray tube 101. The filament current generator supplies a filament current to the cathode filament of the X-ray tube 101.

The gantry 12 contains a rotation support mechanism. The rotation support mechanism includes a rotating ring 102, a ring support mechanism that supports the rotating ring 102 so that the rotating ring 102 freely rotates about a rotating shaft R, and a driving unit 106 that drives the ring to rotate.

The X-ray tube 101, and an X-ray detection unit 103 of a two-dimensional array type or a multi-array type are mounted within the rotating ring 102. At the time of imaging or scanning, an object is set on a top 107 and inserted into a cylindrical imaging region 105 between the X-ray tube 101 and the X-ray detection unit 103 in the gantry 12. A data acquisition unit 109 is connected to the output side of the X-ray detection unit 103. Data acquired by the data acquisition unit 109 are stored in the data storage unit 14 via a non-contact data transmission unit 111.

Upon receiving application of a voltage (to be referred to as a tube voltage hereinafter) and supply of a filament current via a slip ring 113 from the high-voltage generation unit 10, the X-ray tube 101 emits X-rays from an X-ray focus 115. The X-rays emitted from the X-ray focus 115 are shaped into, e.g., a cone beam shape (pyramid shape) by a collimator unit 117 attached to the X-ray radiation window of the X-ray tube 101. An X-ray radiation range 119 is indicated by a dotted line in FIG. 1. The X-ray tube 101 according to the embodiment is assumed to be a rotating anode X-ray tube. Note that even an X-ray tube of another type other than the rotating anode X-ray tube is also applicable to the embodiment. The high-voltage generation unit 10 and the X-ray tube 101 will be collectively called an X-ray generation unit. Note that this embodiment concerns an X-ray computed tomography apparatus 1 based on photon counting, so an X-ray generated by the X-ray generation unit will be called an X-ray photon.

The X-ray detection unit 103 is attached at a position and angle at which it faces the X-ray tube 101 via the rotating shaft R. The X-ray detection unit 103 includes a plurality of X-ray detection elements for photon counting. The plurality of X-ray detection elements are arrayed two-dimensionally. In this description, a single X-ray detection element constitutes a single channel. Of array directions of the X-ray detection elements, a direction parallel to the rotating shaft R is defined as the X-axis, and a direction perpendicular to the rotating shaft R and the X-axis is defined as the Y-axis. A channel number and an X-ray detection element number are defined by, e.g., coordinates along the X- and Y-axes (to be referred to as X- and Y-coordinates hereinafter). Each of the plurality of X-ray detection elements includes a scintillator and a photodetection element. The scintillator is arranged on the front surface of the photodetection element. That is, the photodetection element is provided on the rear surface of the scintillator. X-ray photons that have been generated by the X-ray tube 101 and have passed through the object enter the scintillator. The scintillator generates scintillation light upon receiving the X-ray photons. The scintillation light is emitted for a scintillator-specific time (e.g., $40 \times 10^{-9}$ s). More specifically, the scintillator generates a plurality of scintillation photons in accordance with the energy of the X-ray photons.

The photodetection element generates charges based on the scintillation photons. The photodetection element includes a photoelectric conversion element, a readout circuit, and an operational amplifier (none are shown). The photoelectric conversion element is an element that converts light into charges. More specifically, the photoelectric conversion element is, e.g., a photodiode or a photo multiplier tube: to be referred to as a PMT hereinafter).

To simplify the description, the photoelectric conversion element is a photodiode. A case in which the photoelectric conversion element is a PMT will be explained later. The photodiode includes a p-type layer, an n-type layer, and a light absorption layer. When scintillation photons enter the light absorption layer of the photodiode, the light absorption layer generates electron-hole pairs. By a voltage (internal voltage) applied in advance to the photodiode, the holes drift to the p-type layer side, and the electrons drift to the n-type layer side. The speed at which electrons drift in the light absorption layer will be called a drift speed. Note that the drift speed may be the speed of holes drifting in the light absorption layer. Charges thus generated by scintillation photons are accumulated in a capacitor connected to the photodiode. A readout circuit (to be described later) is connected to the capacitor.

The PMT includes a photoelectric surface, an electron multiplier, and an anode. The photoelectric surface generates photoelectrons by incident scintillation light. The electron multiplier multiplies the generated photoelectrons to generate a plurality of electrons. The anode is connected to a capacitor that accumulates a plurality of electrons. The capacitor is connected to the readout circuit. A plurality of electrons are read out as a current. Note that the PMT may be a silicon PMT made of silicon.

The readout circuit reads out charges accumulated in the capacitor in a predetermined cycle (e.g., $10^{-12}$ sec). The readout circuit outputs the readout charges to an operational amplifier (to be described later). The operational amplifier converts the readout charges into a voltage signal. The operational amplifier outputs, as an output signal, the voltage signal to the peak value detection unit of the data acquisition unit 109 (to be described later).

As shown in FIG. 2, the data acquisition unit 109 includes a peak value detection unit 120, a peak value storage unit 122, a characteristic determination unit 124, a peak value correction unit 126, an analog to digital converter (to be referred to as an ADC hereinafter) 128, and a counter 130.

Based on an output signal from a photodetection element 104, the peak value detection unit 120 detects a plurality of peak values corresponding to respective X-ray photons entering the scintillator. More specifically, every time a voltage signal is input from the operational amplifier, the peak value detection unit 120 calculates a difference value by subtracting an immediately preceding input voltage signal from the input voltage signal. When the difference value changes from positive to negative (to be referred to as local maximum time hereinafter), the peak value detection unit 120 outputs the input voltage signal to the peak value storage unit 122 (to be described later). The peak value detection unit 120 outputs the local maximum time to the characteristic determination unit 124 (to be described later) as the time when an X-ray photon was detected. When the difference value is negative and is lower than a predetermined threshold, the peak value detection unit 120 outputs, to the peak value storage unit 122, a reset signal for resetting a peak value stored in the peak value storage unit 122. Note that the peak value detection unit 120 may output, to the peak value storage unit 122, a voltage signal obtained when the difference value exceeded the threshold.

The peak value storage unit 122 stores a plurality of peak values detected by the peak value detection unit 120. Of the plurality of peak values stored in the peak value storage unit 122, the second and subsequent peak values are output to the peak value correction unit 126 (to be described later). Note that a plurality of peak hold circuits can also be substituted for the functions of the peak value detection unit 120 and peak value storage unit 122. At this time, once each peak hold circuit stores a peak value, it keeps storing the peak value until a reset signal is obtained. That is, the number of peak hold circuits corresponds to the number of peak values to be stored. Note that the peak value storage unit 122 may store a voltage signal when the difference value exceeds the threshold.

To simplify the description, the peak value storage unit 122 is assumed to store two peak values (to be referred to as first and second peak values hereinafter) in an output signal. The first peak value is a peak value corresponding to the first X-ray photon entering the scintillator. The second peak value is a peak value corresponding to the second X-ray photon entering the scintillator while scintillation light by the first X-ray photon attenuates. That is, the first peak value and the second peak value are peak values detected based on an output signal regarding pile-up. Note that the peak value storage unit 122 can store a plurality of peak values when pile-up occurs.

An output signal from the photodetection element 104 along with pile-up will be described in detail. When an X-ray photon newly enters the scintillator in the scintillation light attenuation period, the amount of charges accumulated in the capacitor of the photoelectric conversion element is the sum of charges regarding the first X-ray photon previously entering the scintillator, and charges regarding the second X-ray photon newly entering the scintillator in the scintillation light attenuation period. Thus, an output signal from the operational amplifier is the sum of output signals derived from the first and second X-ray photons. Out of the overlap of the output signals by the first and second X-ray photons in the scintillation light attenuation period, the attenuation characteristic of the output signal based on attenuation of scintillation light by the first X-ray photon will be called the attenuation characteristic of scintillation light.

More specifically, the attenuation characteristic of scintillation light is defined as a function $f(t_2-t_1)$ of a time $(t_2-t_1)$ between time (to be referred to as first detection time hereinafter) $t_1$ when the first X-ray photon was detected, and time (to be referred to as second detection time hereinafter) $t_2$ when the second X-ray photon was detected. The function f is a function representing attenuation of scintillation light.

Note that when a plurality of X-ray photons enter the scintillator during the scintillation light attenuation period, the attenuation characteristic of the scintillation light is defined, e.g., as follows. Letting $t_n$ be the detection time of the nth X-ray photon entering the scintillator, and $t_{n+1}$ be the detection time of the (n+1)th X-ray photon entering the scintillator during the nth scintillation light attenuation period, the attenuation characteristic of scintillation light is given by the function $f(t_{n+1}-t_n)$.

The concrete shape of the function f representing the attenuation characteristic of scintillation light is defined, e.g., as follows. When the number of scintillation components in the scintillator is one, the function f is defined by, e.g., $$f(t_{n+1}-t_n)=\alpha \times \exp\{-(t_{n+1}-t_n)\times \beta\}+\gamma$$

where $\alpha$, $\beta$, and $\gamma$ are the scintillator-specific constants. The scintillation component corresponds to an attenuation time constant for discriminating the attenuation characteristic of scintillation light. When the scintillation component, i.e., the attenuation time constant changes, scintillation light exhibits a different attenuation characteristic. In the above equation, the attenuation time constant is $1/\beta$.

When the number of scintillation components is two, function f is defined by, e.g., $$f(t_{n+1}-t_n)=\alpha_1 \times \exp\{-(t_{n+1}-t_n)\times \beta_1\}+\gamma_1+\alpha_2 \times \exp\{-(t_{n+1}-t_n)\times \beta_2\}+\gamma_2$$

where $\alpha_1$, $\beta_1$, $\gamma_1$, $\alpha_2$, $\beta_2$, and $\gamma_2$ are the scintillator-specific constants. In the above equation, the attenuation time constants are $1/\beta_1$ and $1/\beta_2$.

In general, when the number of scintillation components is m, the function f is defined by, e.g., $$f(t_{n+1}-t_n)=\Sigma[\alpha_i \times \exp\{-(t_{n+1}-t_n)\times \beta_i\}+\gamma_i]$$

where the summation sign $\Sigma$ is the sum from i=1 to i=m, and $\alpha_1$, $\beta_1$, and $\gamma_1$ are the scintillator-specific constants. In the above equation, the attenuation time constant is $1/\beta_i$, and there are m components.

FIG. 3 is a view showing an example of pile-up. Since the next X-ray photon enters (b) the scintillator at a time point (a) when scintillation light has not attenuated sufficiently, an output from the photodetection element increases at the overlap of output signals, as shown in FIG. 3.

In addition, when pile-up occurs, a charge amount arising from the second X-ray photon decreases in comparison with a charge amount generated when no pile-up occurs. As a result, the peak value of an output signal from the photodetection element 104 decreases. The reason of the decrease of the peak value will be explained by exemplifying a photodiode as the photoelectric conversion element in the photodetection element 104. Note that the decrease of the peak value by pile-up when the photoelectric conversion element is a PMT will be described in detail later.

When scintillation light derived from the second X-ray photon enters the photodiode during a value (to be referred to as a drift time hereinafter) obtained by dividing the distance between the p-type layer and the n-type layer in the photodiode by the drift speed of electrons, electron-hole pairs are newly generated. If electrons moving at the drift speed collide against the newly generated holes, pair annihilation occurs. Accordingly, charges, which should originally move to the n-type layer side and be accumulated, decrease. The decrease of charges to be accumulated leads to a decrease of the peak value of an output signal.

When the photoelectric conversion element is a PMT, the decrease of the peak value by pile-up occurs as follows. The capacitor voltage becomes lower than a predetermined baseline in the readout period of charges accumulated in the PMT. The decreased capacitor voltage recovers to the predetermined baseline by recharging for a predetermined time. When charges arising from the second X-ray photon are accumulated in the capacitor within the predetermined time, the peak value in the output signal decreases because the decreased capacitor voltage has not recovered to the baseline.

The drift time and the predetermined time will be collectively called an output decreased period. A characteristic representing the degree of a decrease of the peak value regarding the second X-ray photon in an output signal from the photodetection element when the second X-ray photon enters the scintillator to cause pile-up in the output decreased period generated by the first X-ray photon entering the scintillator will be called an output decreased characteristic.

More specifically, the output decreased characteristic is defined as follows. Let $B_1$ be a peak value corresponding to the first X-ray photon, and $B_{max}$ be the maximum value of a signal that can be output from the photodetection element 104. Then, the output decreased characteristic is defined by a function $g(t_2-t_1, B_1/B_{max})$ using a time interval $(t_2-t_1)$ between first detection time $t_1$ and second detection time $t_2$, and a ratio $(B_1/B_{max})$ of $B_1$ to $B_{max}$. That is, the function g is a function reflecting the output decreased characteristic (dead characteristic) of the photodetection element. The concrete shape of the function g is, e.g., $g(t_2-t_1, B_1/B_{max}) = (B_1/B_{max}) \times \exp((t_2-t_1)/T)$, where T is the output decreased period. The shape of the function g representing the output decreased characteristic of the photodetection element generally depends on the photoelectric conversion element, the readout circuit, and the circuit regarding the operational amplifier in the photodetection element 104. For this reason, the shape of the function g is not limited to the above-mentioned function shape.

When a plurality of X-ray photons enter the scintillator in the output decreased period, the output decreased characteristic is defined, e.g., as follows. Letting $t_n$ and $B_n$ be the detection time and peak value of the nth X-ray photon entering the scintillator, and $t_{n+1}$ be the detection time of the (n+1)th X-ray photon entering the scintillator in the nth output decreased period, the output decreased characteristic is, e.g., $g(t_{n+1}-t_n, B_n/B_{max})$, e.g., $g(t_{n+1}-t_n, B_n/B_{max}) = (B_n/B_{max}) \times \exp((t_{n+1}-t_n)/T)$. The shape of the function g representing the output decreased characteristic of the photodetection element generally depends on the photoelectric conversion element, the readout circuit, and the circuit regarding the operational amplifier in the photodetection element 104. Hence, the shape of the function g is not limited to the above-mentioned function shape.

The characteristic determination unit 124 determines the attenuation characteristic of scintillation light by each of a plurality of X-ray photons, and the output decreased characteristic of the photodetection element 104 based on the time when each of a plurality of peak values was detected, and the plurality of peak values stored in the peak value storage unit 122. The characteristic determination unit 124 outputs the determined attenuation characteristic and output decreased characteristic to the peak value correction unit 126 (to be described later).

More specifically, the characteristic determination unit 124 stores a value (to be referred to as an attenuation ratio hereinafter) indicating an attenuation characteristic with respect to the first time and the second time, that is, the first correspondence table of the value of the function f. The attenuation ratio is a ratio at which an output signal regarding the first X-ray photon is reduced in the time between the first detection time and the second detection time with respect to the first peak value $B_1$. The characteristic determination unit 124 determines an attenuation ratio based on the first time, the second time, and the first correspondence table.

The characteristic determination unit 124 stores a value (to be referred to as an output decreased ratio hereinafter) indicating an output decreased characteristic with respect to the first time, the second time, and the first peak value, that is, the second correspondence table of the value of the function g. The output decreased ratio is a ratio at which the ratio of the first peak value to the maximum value of a signal that can be output from the photodetection element 104 decreases in the time between the first detection time and the second detection time with reference to the output decreased period. The characteristic determination unit 124 determines an output decreased ratio based on the first time, the second time, the first peak value, and the second correspondence table. Note that the output decreased ratio may be appropriately set in advance in accordance with the type of photoelectric conversion element.

The peak value correction unit 126 corrects a second peak value $B_2$ by using the attenuation characteristic (attenuation ratio) $f(t_2-t_1)$ and output decreased characteristic (output decreased ratio) $g(t_2-t_1, B_1/B_{max})$ that are determined in the characteristic determination unit 124, and the first peak value $B_1$. The relation between a corrected second peak value $A_2$, the attenuation ratio $f(t_2-t_1)$, the output decreased ratio $g(t_2-t_1, B_1/B_{max})$, the first peak value $B_1$, and the second peak value $B_2$ is given as, e.g., $A_2 = B_2/(1-g(t_2-t_1, B_1/B_{max})) - B_1 \times f(t_2-t_1)$.

More specifically, the corrected second peak value $A_2$ may be given by $(B_2 - B_1 \times f(t_2-t_1))/(1-g(t_2-t_1, B_1/B_{max}))$. That is, the corrected second peak value $A_2$ is given by:

$$A_2 = (B_2 - B_1 \times f(t_2 - t_1))/(1 - g(t_2 - t_1, B_1/B_{max}))$$
$$= B_2/(1 - g(t_2 - t_1, B_1/B_{max})) -$$
$$B_1 \times f(t_2 - t_1)/(1 - g(t_2 - t_1, B_1/B_{max})).$$

Figure 4:
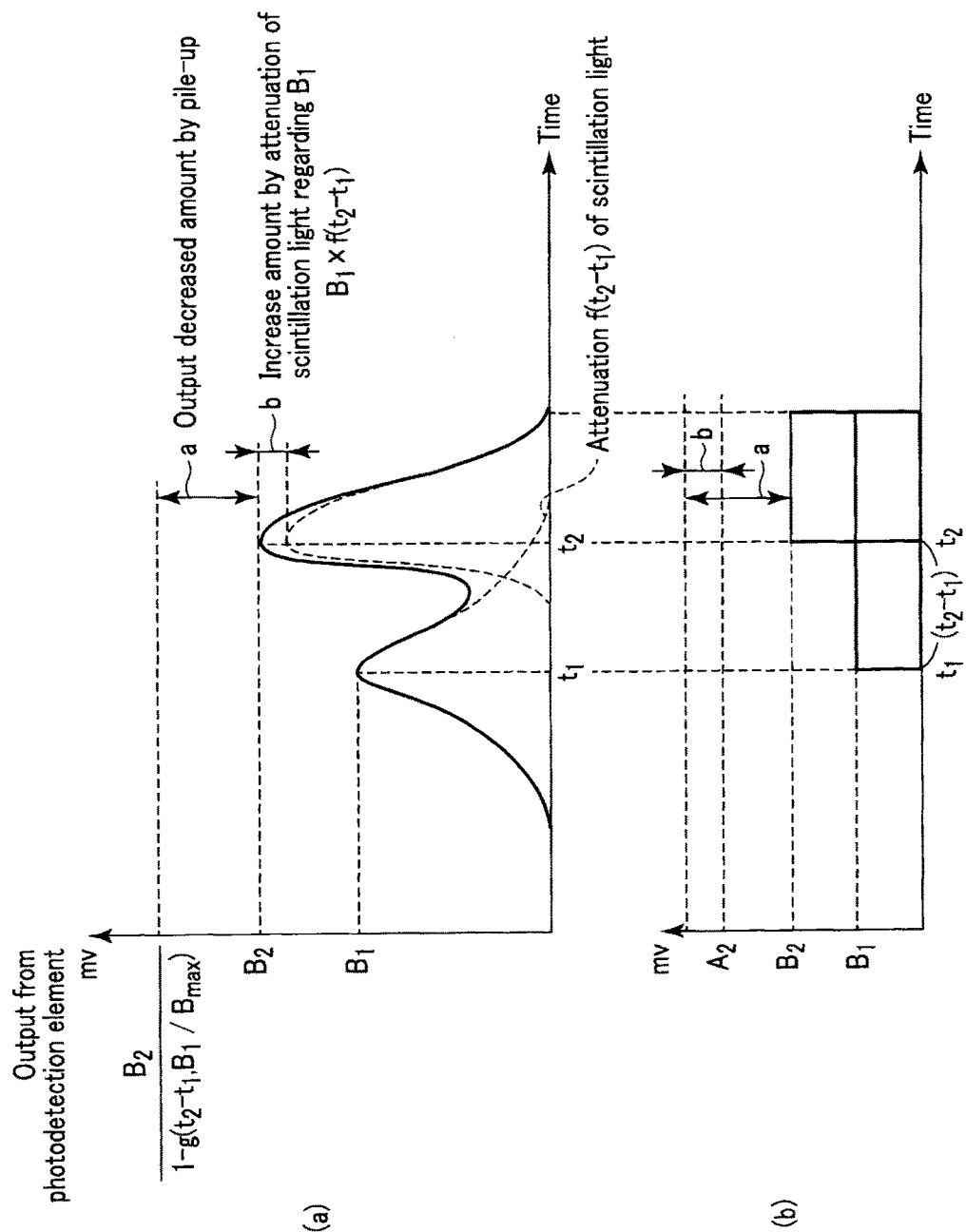
FIG. 4 is a graph showing the first and second peak values in an output from a photodetection element, the first and second peak values stored in a peak value storage unit, and the corrected second peak value according to the embodiment.

The first term in the above equation corresponds to increasing the peak value $B_2$ by an output decreased amount a generated by pile-up in (a) of FIG. 4. The second term in the above equation represents an output increase amount b by attenuation of scintillation light regarding the peak value $B_1$ in (a) of FIG. 4.

More specifically, the peak value correction unit 126 stores the third correspondence table of the attenuation ratio $f(t_2-t_1)$, the output decreased ratio $g(t_2-t_1, B_1/B_{max})$, the first and second peak values, and the second peak value $A_2$. The peak value correction unit 126 determines the corrected second peak value $A_2$ by using the attenuation ratio $f(t_2-t_1)$, the output decreased ratio $g(t_2-t_1, B_1/B_{max})$, the first and second peak values, and the third correspondence table. The peak value correction unit 126 outputs the corrected second peak value $A_2$ to the ADC 128 (to be described later).

When pile-up arises from a plurality of X-ray photons, the peak value correction unit 126 corrects a peak value $B_{n+1}$ by using the attenuation characteristic (attenuation ratio) $f(t_{n+1}-t_n)$ and output decreased characteristic (output decreased ratio) $g(t_{n+1}-t_n, B_n/B_{max})$ that are determined in the characteristic determination unit 124, and the peak value $B_n$. The relation between a corrected peak value $A_{n+1}$, the attenuation ratio $f(t_{n+1}-t_n)$, the output decreased ratio $g(t_{n+1}-t_n, B_n/B_{max})$, and the peak values $B_n$ and $B_{n+1}$ is given as, e.g., $A_{n+1} = B_{n+1}/(1-g(t_{n+1}-t_n, B_n/B_{max})) - B_n \times f(t_{n+1}-t_n)$.

More specifically, the corrected peak value $A_{n+1}$ may be given by $(B_{n+1} - B_n \times f(t_{n+1}-t_n))/(1-g(t_{n+1}-t_n, B_n/B_{max}))$. That is, the corrected peak value $A_{n+1}$ is given by:

$$A_{n+1} = (B_{n+1} - B_n \times f(t_{n+1} - t_n))/(1 - g(t_{n+1} - t_n, B_n/B_{max}))$$
$$= B_{n+1}/(1 - g(t_{n+1} - t_n, B_n/B_{max})) - B_n \times f(t_{n+1} - t_n)/$$
$$(1 - g(t_{n+1} - t_n, B_n/B_{max})).$$

The first term in the above equation corresponds to increasing the peak value $B_{n+1}$ by an output decreased amount generated by pile-up. The second term in the above equation represents an output increase amount by attenuation of scintillation light regarding the peak value $B_n$. When pile-up regarding $B_{n+1}$ influences $B_n$ and pile-up regarding $B_{n-1}$ does not influence $B_n$ the peak value $A_n$ obtained by correcting $B_n$ is given by $B_n/(1-g(t_{n+1}-t_n, B_n/B_{max}))$.

FIG. 4 is a graph showing the first and second peak values in an output from the photodetection element, the first and second peak values stored in the peak value storage unit 122, and the corrected second peak value. The first peak value $B_1$ is detected at the first detection time $t_1$ and stored in the peak value storage unit 122. The second peak value $B_2$ is detected at the second detection time $t_2$ and stored in the peak value storage unit 122. In FIG. 4, a represents an output decreased amount by pile-up. The output decreased amount a is $B_2/(1-g(t_2-t_1, B_1/B_{max}))-B_2$. In FIG. 4, b represents a peak value increase amount by attenuation of scintillation light regarding $B_1$, and represents $B_1 \times f(t_2-t_1)$. Based on these amounts, the corrected second peak value $A_2$ is determined.

The ADC 128 converts the first peak value and the corrected peak value into digital signals (pulses). The counter 130 counts the numbers of X-ray photons respectively corresponding to corrected peak values. The counter 130 outputs the counted number of X-ray photons to the data storage unit 14 via the non-contact data transmission unit 111 in association with the energy of the X-ray photons corresponding to the corrected peak values, the X- and Y-coordinates of the X-ray detection element, and the view angle. Note that a plurality of energy bins may replace the energy of X-ray photons. At this time, a plurality of counts respectively included in the respective energy bins are added.

Figure 5:
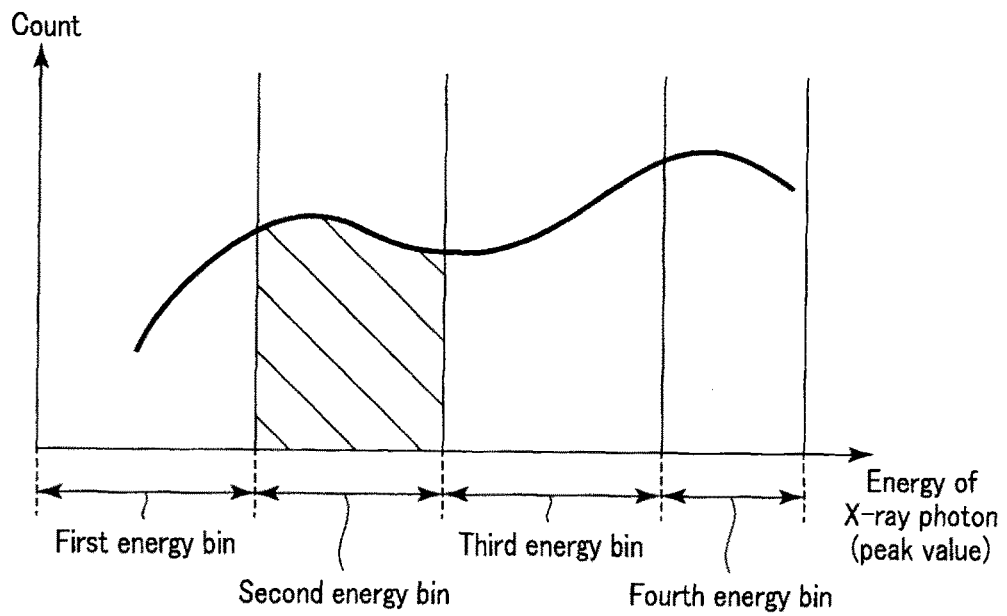
FIG. 5 is graph showing an example of the count with respect to the energy of the X-ray photon according to the embodiment.

FIG. 5 is a graph showing an example of the count with respect to the energy of X-ray photons in one X-ray detection element positioned at a given view angle. In FIG. 5, the abscissa is divided into the first to fourth energy bins. For example, the count in the second energy bin is the sum of counts in a hatched region in FIG. 5. That is, when there are four types of energy bins, the data acquisition unit 109 can acquire data based on four types of counts from an output from one X-ray detection element at a given view angle. Note that the number of energy bins is not limited to four and is arbitrary.

The data storage unit 14 stores list mode data formed from the view angle, the X- and Y-coordinates of the X-ray detection element, the energy of X-ray photons, and the count. Note that the data storage unit 14 may store sinogram data formed from the view angle, the channel number, and the count for each energy of X-ray photons.

The reconstruction unit 16 reconstructs a medical image based on a list mode data set or sinogram data set corresponding to one round of an object that is stored in the data storage unit 14. The reconstruction unit 16 can reconstruct a plurality of medical images corresponding to energies of X-ray photons. When there are four types of energy bins, the reconstruction unit 16 can reconstruct four medical images based on the list mode data set or sinogram data set corresponding to one round of the object.

The display unit 18 displays an image reconstructed by the reconstruction unit 16, conditions set for X-ray computed tomography, and the like.

The input unit 20 inputs the imaging conditions of X-ray computed tomography desired by the operator, information of an object, and the like. More specifically, the input unit 20 inputs various instructions, commands, information, selections, and settings from the operator into the X-ray computed tomography apparatus 1. Although not shown, the input unit 20 includes a track ball for performing setting of a region of interest or the like, a switch button, a mouse, and a keyboard. The input unit 20 detects the coordinates of a cursor displayed on the display screen, and outputs the detected coordinates to the control unit 22. Note that the input unit 20 may be a touch panel provided to cover the display screen. In this case, the input unit 20 detects coordinates indicated by a touch according to a coordinate reading principle such as an electromagnetic induction method, an electromagnetic distortion method, or a pressure sensing method, and outputs the detected coordinates to the control unit 22.

The control unit 22 functions as the center of the photon counting X-ray computed tomography apparatus 1. The control unit 22 includes a CPU and a memory (neither is shown). The control unit 22 controls a bed (not shown), the gantry, and the high-voltage generation unit 10 for X-ray computed tomography based on inspection schedule data and control programs stored in the memory (not shown). More specifically, the control unit 22 temporarily stores, in the memory (not shown), pieces of information such as an instruction from the operator, the conditions of image processing, and the like that are sent from from the input unit 20. Based on these pieces of information temporarily stored in the memory, the control unit 22 controls the bed, the gantry, and the high-voltage generation unit 10. The control unit 22 reads out, from a storage unit (not shown), a control program for executing generation, display, and the like of a predetermined image, loads the program in the memory of the control unit 22, and executes calculation, processing, and the like regarding various processes.

(Peak Value Correction Function)

The peak value correction function is a function of correcting a plurality of peak values in accordance with an attenuation characteristic and output decreased characteristic determined based on the time when each of a plurality of peak values was detected, and the plurality of peak values. Processing (to be referred to as peak value correction processing hereinafter) complying with the peak value correction function will be explained.

Figure 6:
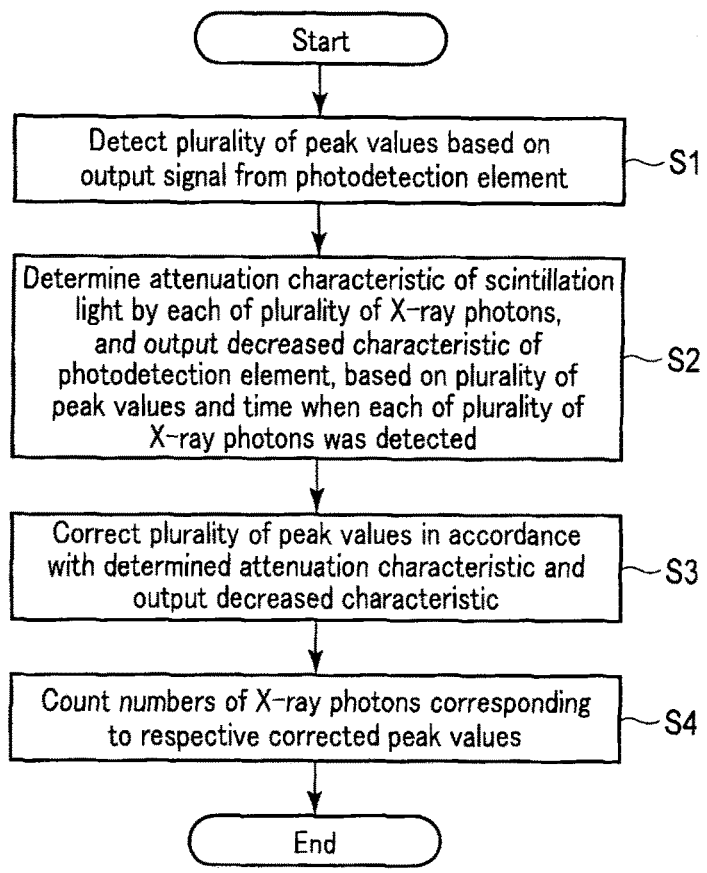
FIG. 6 is flowchart showing an example of the procedures of peak value correction processing according to the embodiment.

FIG. 6 is a flowchart showing an example of the procedures of peak value correction processing.

A plurality of peak values are detected based on an output signal from the photodetection element 104 (step S1). The time when each of the plurality of peak values was detected is output to the characteristic determination unit 124. An attenuation characteristic and output decreased characteristic are determined based on the time when each of the plurality of peak values was detected, and the plurality of peak values (step S2). Each of the plurality of peak values is corrected in accordance with the determined attenuation characteristic and output decreased characteristic (step S3). The numbers of X-ray photons corresponding to the respective corrected peak values are counted (step S4).

The above-described arrangement can yield the following effects.

The X-ray computed tomography apparatus 1 according to the embodiment can correct a peak value regarding each X-ray photon in order to discriminate each X-ray photon with respect to an output signal regarding pile-up generated by a plurality of X-ray photons, and calculate the energy of each X-ray photon. That is, the X-ray computed tomography apparatus 1 can determine the attenuation characteristic of scintillation light based on the time when each of the plurality of peak values was detected, and the plurality of peak values. In addition, the X-ray computed tomography apparatus 1 can determine the output decreased characteristic of the photodetection element 104 based on the time when each of the plurality of peak values was detected, and the plurality of peak values. In accordance with the determined attenuation characteristic and output decreased characteristic, the X-ray computed tomography apparatus 1 can correct each of the plurality of peak values contributing to pile-up into a peak value corresponding to the energy of a related X-ray photon.

From this, the X-ray computed tomography apparatus 1 can use a count regarding X-ray photons contributing to pile-up for an output signal regarding pile-up. Therefore, a high counting rate can be obtained even in the arrangement in which the photodetection element 104 is combined with the scintillator.

Note that each function according to each embodiment can be implemented by installing programs for executing the processing in a computer such as a workstation, and loading them into the memory. At this time, the programs capable of causing the computer to execute the method can be distributed by storing them in a storage medium such as a magnetic disk (Floppy® disks, hard disks, or the like), an optical disk (CD ROM, DVD, and the like), or a semiconductor memory.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube configured to generate an X-ray;
an X-ray detector including a scintillator configured to generate scintillation light upon incidence of a plurality of X-ray photons that have been generated from the X-ray tube and have passed through an object, and a photodetection element provided on a rear surface of the scintillator;
a peak value detector configured to detect a plurality of peak values corresponding to respective X-ray photons entering the scintillator based on an output signal from the photodetection element;
processing circuitry configured to determine an attenuation characteristic of the scintillation light by each of the plurality of X-ray photons and an output decreased characteristic of the photodetection element, based on the peak values and time when each of the plurality of peak values was detected, and to correct the plurality of detected peak values in accordance with the attenuation characteristic and the output decreased characteristic; and
a counter configured to count the numbers of X-ray photons corresponding to the respective corrected peak values;
wherein the processing circuitry is configured to reconstruct a medical image based on an output from the counter.

2. The X-ray computed tomography apparatus according to claim 1, wherein the processing circuitry is configured to determine the attenuation characteristic and the output decreased characteristic, based on the peak values and a time interval between the time and time when the peak value was detected immediately before the time when each of the peak values was detected.

3. The X-ray computed tomography apparatus according to claim 1, wherein the output decreased characteristic is a characteristic representing a degree of a decrease of a ratio of each of the plurality of peak values to a maximum value that can be output from the photodetection element.

4. The X-ray computed tomography apparatus according to claim 1, wherein the output decreased characteristic is a characteristic representing a degree of a decrease of the output signal by recharging of the photodetection element.

5. The X-ray computed tomography apparatus according to claim 1, wherein the processing circuitry is configured to store the output decreased characteristic in accordance with a type of a photoelectric conversion element in the photodetection element.

6. A photon counting method comprising:
detecting a plurality of peak values corresponding to respective X-ray photons entering a scintillator;
determining an attenuation characteristic of scintillation light by each of the plurality of X-ray photons and an output decreased characteristic of a photodetection element based on the peak values and time when each of the plurality of peak values corresponding to the respective X-ray photons was detected, and;
correcting the plurality of detected peak values in accordance with the attenuation characteristic and the output decreased characteristic; and
counting the numbers of X-ray photons corresponding to the respective corrected peak values.

7. The photon counting method according to claim 6, wherein the determining the attenuation characteristic and the output decreased characteristic is determining the attenuation characteristic and the output decreased characteristic based on the peak values and a time interval between the time and time when the peak value was detected immediately before the time.

8. The photon counting method according to claim 6, wherein the output decreased characteristic is a characteristic representing a degree of a decrease of a ratio of each of the plurality of peak values to a maximum value that can be output from the photodetection element.

9. The photon counting method according to claim 6, wherein the output decreased characteristic is a characteristic representing a degree of a decrease of the output signal from the photodetection element by recharging of the photodetection element.

10. The photon counting method according to claim 6, further comprising storing the output decreased characteristic in accordance with a type of a photoelectric conversion element in the photodetection element.

* * * * *